United States Patent [19]

Zaruba et al.

[11] 4,435,915
[45] Mar. 13, 1984

[54] HANGING DOLL HOUSE STRUCTURE

[75] Inventors: John V. Zaruba; Rouben T. Terzian, both of Chicago, Ill.

[73] Assignee: Marvin Glass & Associates, Chicago, Ill.

[21] Appl. No.: 340,969

[22] Filed: Jan. 20, 1982

[51] Int. Cl.³ .......................................... A63H 33/00
[52] U.S. Cl. ......................................... 46/12; 40/539; 40/617; 46/116
[58] Field of Search ..................... 46/12, 13, 116, 153, 46/18, 19, 21, 32; 40/617, 539; 217/10

[56] References Cited

U.S. PATENT DOCUMENTS

| | | | |
|---|---|---|---|
| 2,593,218 | 4/1952 | Swain | 46/116 X |
| 2,621,010 | 12/1952 | White | 46/32 X |
| 2,682,727 | 7/1954 | Keljik | 46/12 |
| 3,120,078 | 2/1964 | Bessinger | 46/21 X |
| 3,271,895 | 9/1966 | Sorensen | 46/21 X |
| 3,309,805 | 3/1967 | Thomas | 40/617 |
| 3,719,001 | 3/1973 | Archer | 46/12 |
| 3,955,307 | 5/1976 | Payton | 46/12 |

OTHER PUBLICATIONS

Hinson, D. A., *Quilting Manual,* pub. by Hearthside Press, Inc., N.Y.C., Illustration of Authors "Doll House" Quilt.

*Primary Examiner*—F. Barry Shay

[57] ABSTRACT

A collapsible doll house for displaying and storing toy dolls includes a housing defined by a top wall, a front wall and first and second side walls. At least one floor member is secured to the housing and a plurality of openings are defined in the top and front walls within which may be positioned toy dolls. One or more elastic or vinyl members are secured to the first and second side walls for retaining additional toy dolls. The housing further includes at least one member allowing the housing to be mounted on a wall or similar structure. Indicia is included on the outside of the housing to depict a predetermined theme.

6 Claims, 5 Drawing Figures

U.S. Patent      Mar. 13, 1984      4,435,915
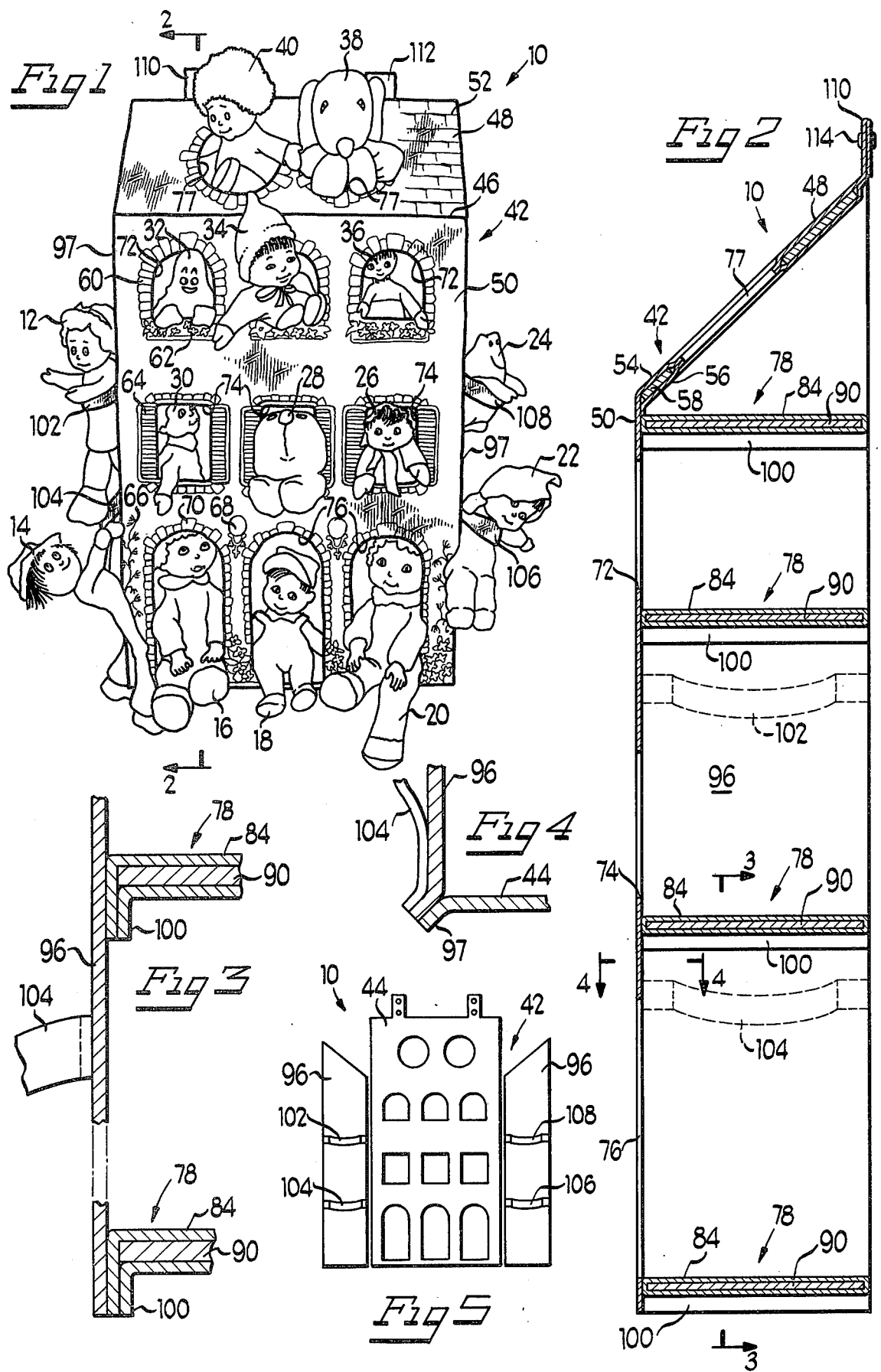

HANGING DOLL HOUSE STRUCTURE

BACKGROUND OF THE INVENTION

A. Field of the Invention

The present invention relates to doll houses and in particular to a new and improved case for storing and displaying toy dolls and the like.

B. Description of the Prior Art

Many individuals collect and own a large number of toy dolls or similar items. Due to the number and size of the toy dolls, it is often difficult to provide a device for storing these dolls in a manner such that they are not damaged. A typical prior art storage case is a box or similar type device in which the dolls are stacked. This type of storage can result in damage to the dolls as well as making it difficult to locate a particular doll when desired. In addition, the typical prior art storage case of this type does not display the doll nor does it provide a decorative appearance for the user. These prior art storage cases also suffer the disadvantage that they are best placed on a shelf or stored in a closet out of sight.

SUMMARY OF THE INVENTION

An object of the present invention is to provide a new and improved doll house for storing and displaying toy dolls and augmenting doll play activities.

Briefly, the present invention is directed to a new and improved collapsible doll house for storing and displaying toy dolls and the like. The doll house includes a housing defined by top and front walls and a pair of side walls. A plurality of openings are defined in the walls and at least one floor is positioned within the housing. The dolls may be placed within the openings. Elastic members are secured to the sides of the housing and one or more toy dolls may be placed within these elastic members and held in position. At least one member for hanging the housing on the wall is also included such that the case may be mounted on a wall to display the dolls carried therein.

BRIEF DESCRIPTION OF THE DRAWING

The above and other objects and advantages and novel features of the present invention will become apparent from the following detailed description of the preferred embodiment of the invention illustrated in the accompanying drawing wherein:

FIG. 1 is a front elevational view of one embodiment of the present invention;

FIG. 2 is an enlarged cross sectional view taken generally along the line 2—2 in FIG. 1;

FIG. 3 is a partial cross-sectional view taken generally along line 3—3 of FIG. 2;

FIG. 4 is a cross-sectional view taken generally along line 4—4 of FIG. 2; and

FIG. 5 is a reduced exploded view of the components of the case prior to assembly.

BRIEF DESCRIPTION OF THE PREFERRED EMBODIMENT

Referring to the drawing there is illustrated a doll house generally designated by the reference numeral 10 for storing and displaying a plurality of dolls 12, 14, 16, 18, 20, 22, 24, 26, 28, 30, 32, 34, 36, 38, and 40. The doll house 10 is fabricated at least in part of a pliant material, conveniently heat sealable pliant material such as vinyl or the like, allowing the doll house 10 to be collapsed and easily stored when not in use. While being used the doll house 10 may be hung on a wall or similar structure and functions not only to store the dolls 12-40 but in addition, as an amusement device that augments doll playing activities.

The case 10 includes a housing generally designated by the reference numeral 42 that includes a single planar wall 44 that may be folded along a fold line 46 to define a roof 48 and a front wall 50. The roof 48 may include indicia 52 thereon that depicts shingles or similar roofing material. As shown in FIG. 2 the roof 48 includes first 54 and second 56 layers of pliant material such as vinyl. Sandwiched between the layers 54 and 56 is a rigid member 58 such as cardboard or the like. The sheet 54 extends downwardly to define the front wall 50 and may include the indicia 60 that provides the appearance of bricks around a window and indicia 62 that depicts a flowerbox. Additional indicia 64 may be included that depicts shutters and indicia 66 that corresponds to vines. Indicia 68 that depicts a lamp and indicia 70 that depicts bricks or stones around a doorway may also be included. The indicia 60, 62, 64, 66 and 70 gives the front wall 50 the appearance of a building such as a hotel or other large building.

A plurality of openings 72, 74, 76, 77 are fabricated in the front wall 50. The openings may be of different configuration such as, for example, the openings 72 that are arch shaped windows, the openings 74 that are square or rectangular shaped windows and the openings 76 that are shaped doorways. There are also round openings 77 in the roof 48. These openings 72, 74, 76 and 77 are adjacent to floor members generally designated by the reference numerals 78, shown in FIGS. 2 and 3. The floor members 78, each include envelopes 84 of pliant material similar to the material defining the layers 54 and 56. Each envelope 84 includes rigid member 90 sandwiched therebetween made for example of cardboard, wood or similar rigid material. The rigid members 90 along with the rigid member 58 functon to provide a frame for the doll house 10 when hung on a wall or the like.

The envelopes 78, as shown in FIG. 3, are secured to the two side walls 96 by heat sealing or a similar technique. The side walls 96, which may also be made of pliant heat sealable material, are in turn secured to the front wall 44 along the peripheral edges 97 thereof. The envelopes 84 are secured to the side walls 96, as shown in FIG. 5, by glue or heat sealing along a flap 100 of the envelope 84. The front wall 44 and the sidewalls 96 are not reinforced by rigid members such as the members 58, 90, allowing the case 10 to be vertically collapsible and thereby capable of being stored in a small space until it is desired to be used.

As illustrated in FIG. 1, the dolls 16, 18, 20, 26, 28, 30, 32, 34, 36, 38 and 40 may be stored and displayed in the doll house 10 by placement within the apertures 72, 74, 76 or 77. The dolls 16-40 are mounted within these openings 72, 74, 76 and 77 and positioned on the floors 78 so as to be easily observed thereby allowing them to be displayed by the doll house 10 in a fanciful manner as residents of a building.

The doll house 10 also provides additional structure for storing and displaying the dolls 12, 14, 22 and 24. This manner of display is provided by elastic straps 102, 104, 106 and 108. The straps 102, 104, 106 and 108, which may be of woven elastic material, as best illustrated in FIG. 4, are secured to the sidewalls 96 at both ends of the straps by adhesive material or a similar method of attachment thereby forming half loops. The dolls 12, 14, 22, and 24 may be positioned within the elastic bands 102, 104, 106 and 108, respectively, and held against the side walls 96 while at the same time offering an interesting display of the dolls 12, 14, 22, and 24.

As can be understood from the above, the doll house 10 provides a novel storage structure but in addition, it may also be used as a display in a room or the like. In order to function as a display the case 10 includes tabs 110 and 112 that are extensions of the sheet material 54. The tabs 110 and 112 are bent over and secured together by grommets 114. The grommets 114 may be slipped over a nail or similar structure in a wall thereby hanging the case 10 on the wall either in view to function as a display case or out of sight such as on the back of a door so as to be hidden but to provide an out of the way place to store the dolls 12-40.

Many other advantages and other uses of the present invention will become obvious in view of this disclosure and therefore, the foregoing detailed description has been given for clearness of understanding only and no unnecessary limitations should be understood threfrom as some modifications will be obvious to those skilled in the art.

What is claimed and sought to be secured by Letters Patent of the United States is:

1. A case for storing and displaying a plurality of toy dolls and the like, comprising:
   a housing including a roof, a front wall a first side wall and a second side wall;
   a plurality of vertically spaced floors mounted in said housing;
   means for displaying the dolls including a plurality of openings in said roof and said front wall, said openings being related to said floors in a manner whereby a floor can support a doll in position for display through an opening;
   a plurality of elastic members secured to said first and second side walls for holding dolls and the like; and
   means for hanging said housing on a wall or the like.

2. The case set forth in claim 1 wherein said hanging means comprises at least one grommet in said housing.

3. The case set forth in claim 1 further comprising indicia on said housing depicting a building.

4. The case set forth in claim 1 wherein said front and said first and second side walls are of a pliant material to allow said housing to be collapsible.

5. The case set forth in claim 1 wherein said front and said first and second side members are collapsible.

6. The case set forth in claim 1 further comprising indicia on said housing depicting a theme.

* * * * *